United States Patent [19]
Imran

[11] Patent Number: 5,964,798
[45] Date of Patent: Oct. 12, 1999

[54] STENT HAVING HIGH RADIAL STRENGTH

[75] Inventor: Mir A. Imran, Los Altos Hills, Calif.

[73] Assignee: CardioVasc, Inc., Menlo Park, Calif.

[21] Appl. No.: 08/991,384

[22] Filed: Dec. 16, 1997

[51] Int. Cl.⁶ .................................................. A61F 2/06
[52] U.S. Cl. .................................................... 623/1
[58] Field of Search ...................... 623/1, 12; 606/191, 606/194, 195, 198

[56] References Cited

U.S. PATENT DOCUMENTS

| | | | |
|---|---|---|---|
| 5,591,197 | 1/1997 | Orth et al. | 623/1 |
| 5,618,301 | 4/1997 | Hauenstein et al. | 623/1 |
| 5,632,771 | 5/1997 | Boatman et al. | 623/12 |
| 5,695,516 | 12/1997 | Fischell et al. | 606/198 |
| 5,697,971 | 12/1997 | Fischell et al. | 623/12 |
| 5,733,303 | 3/1998 | Israel et al. | 623/1 |
| 5,741,327 | 4/1998 | Frantzen | 623/12 |

*Primary Examiner*—Mickey Yu
*Assistant Examiner*—John M. Black
*Attorney, Agent, or Firm*—Harold C. Hohbach; Flehr Hohbach Test Albritton & Herbert, LLP

[57] ABSTRACT

An expandable stent for deployment into a vessel having a lumen therein comprising a cylindrical member having a length and having proximal and distal extremities and being formed of a metal having a wall defining a central bore having a longitudinal axis extending from the proximal extremity to the distal extremity. The cylindrical member has an inside diameter and an outside diameter. The cylindrical member is formed of at least one cylindrical segment. The at least one cylindrical segment has a pattern formed therein which when the stent is expanded is capable of forming a truss formed of serially connected three-sided triangularly-shaped truss members. The pattern includes a first sinusoid extending circumferentially through 360° about the longitudinal axis. The first sinusoid is in the form of a plurality of major elements having first and second interconnected struts having respectively first and second lengths forming first and second sides of the truss members and defining open sides therebetween. Alternate major elements have open sides facing in opposite directions. The pattern also includes a plurality of foldable struts disposed within the open sides of the major elements and secured to the first and second struts of the major elements so that when the stent is expanded, the foldable struts are capable of unfolding to form the third sides of the truss members. The truss members are serially connected to form a continuous truss extending circumferentially of the cylindrical member to provide a stent which when expanded has high radial strength.

7 Claims, 3 Drawing Sheets

STENT HAVING HIGH RADIAL STRENGTH

This invention relates to an expandable stent having high radial strength and more particularly to such a stent for placement in a vessel in a living body.

Stents heretofore have been provided which have been based on a sinusoidal pattern of metal making them easy to expand. However, such a stent has the disadvantage in that it also can be compressed relatively easily, making it possible to be displaced after it has been deployed. Therefore there is need for a new and improved stent which can withstand higher compressive forces.

In general, it is an object of the present invention to provide a stent which can be readily expanded with low pressure and which has high radial strength after deployment to withstand compressive forces.

Another object of the invention is to provide a stent of the above character which can be economically produced.

Additional objects and features of the invention will appear from the following description in which the preferred embodiment is set forth in detail in conjunction with the accompanying drawings.

In general the expandable stent having high radial strength for deployment into a vessel comprises a cylindrical member having a length and having proximal and distal extremities and being formed of a metal having a wall defining a central bore having a longitudinal axis extending from the proximal extremity to the distal extremity, said cylindrical member having an inside diameter and an outside diameter, said cylindrical member being formed of at least one cylindrical segment, said at least one cylindrical segment having a pattern formed therein which when the stent is expanded is capable of forming a truss formed of serially connected three-sided triangularly-shaped truss members, said pattern including a first sinusoid extending circumferentially through 360° about the longitudinal axis, said first sinusoid being in the form of a plurality of major elements having first and second interconnected struts having respectively first and second lengths forming first and second sides of the truss members and defining open sides therebetween, alternate major elements having therein open sides facing in opposite directions, said pattern also including a plurality of folded struts disposed within the open sides of the major elements and secured to the first and second struts of the major elements, and when the stent is expanded, being capable of unfolding to form the third sides of the truss members, said truss members being serially connected to form a continuous truss extending circumferentially of the cylindrical member to provide a stent which when expanded has high radial strength.

Figure 1:
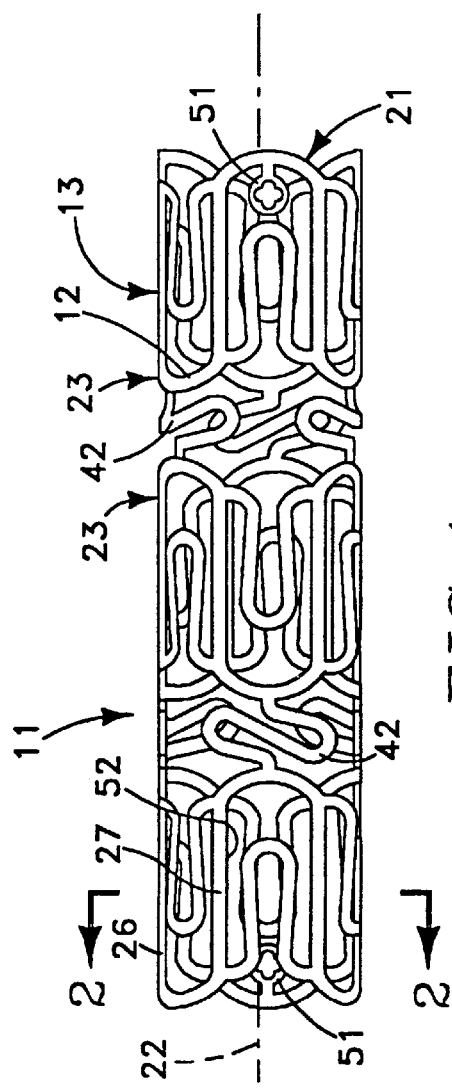
FIG. 1 is a side elevational view of a stent having high radial strength after deployment incorporating the present invention and showing it in an expanded condition.

More in particular as shown in FIG. 1, the stent 11 having high radial strength incorporating the present invention is comprised of at least one segment 12 and preferably a plurality of segments 12 as for example the three segments 12 shown in FIG. 1. Each segment 12 is comprised of a cylindrical member 13. The segment 12 can have a length ranging from 0.050" to 0.100" and preferably a length of approximately 0.060" corresponding to 1.5 mm. The cylindrical member 13 is formed of a suitable material such as stainless steel or alternatively if desired of a shape memory alloy such as Nitinol. The cylindrical member 13 can have a suitable outside diameter as for example 0.030" to 0.100" and preferably an outside diameter of approximately 0.060". The cylindrical member 13 is formed by a wall 14 having a wall thickness ranging from 0.001" to 0.010" and preferably a thickness of 0.003" to provide a lumen 16 extending therethrough having a diameter ranging from 0.020" to 0.200" and preferably a diameter of 0.060".

A pattern 21 is formed in the cylindrical member 13 in a suitable manner such as by laser cutting or alternatively by etching. As shown, the pattern 21 extends in a direction parallel to a longitudinal axis 22 and extends through 360°. This pattern 21 as hereinafter explained when the stent 11 is expanded is capable of forming a truss formed of serially connected three-sided triangularly-shaped truss members. The pattern 21 includes a first sinusoid in the form of a plurality of substantially U-shaped major elements 23 having first and second interconnected struts 26 and 27 having respectively first and second lengths which form first and second sides of three-sided triangularly-shaped truss members 28 (see FIG. 4) with the struts 26 and 27 being common to the struts of adjacent major elements 23 and truss members 28. The struts 26 and 27 define open sides for the truss members 28.

A foldable strut 31 is provided in each of the open sides of the major elements 23 and in the pattern 21 forms a minor element and is generally in the shape of a second sinusoid having first and second interconnected legs 32 and 33 which have their free ends secured to the struts 26 and 27 of the major elements 23 to form minor elements 36.

It can be seen that the first and second sinusoids formed by the major elements 23 and the minor elements 36 both have open sides which face in the same directions which are parallel to the longitudinal axis 22 and that the first and second sinusoids extend through 360° or entirely around the circumference of the cylindrical member 13. As hereinafter explained, the open sided major and minor elements 23 and 36 serve to make the segment 12 expansile in a manner hereinafter described. It also can be seen that alternate open sides face in opposite directions.

When it is desired that the stent 11 have a length which requires use of more than one segment 12, a plurality of segments can be provided in such a stent as shown in FIG. 1 where three segments are shown. Expansile interconnecting means 41 is provided in such a stent and consists of a plurality of circumferentially spaced-apart generally S-shaped links which interconnect the spaced-apart segments 12. The ends of the S-shaped links 42 are secured to major elements 23. As shown in FIG. 1, the segments 12 are circumferentially disposed with respect to each other so that the major elements 23 are generally opposite each other to facilitate interconnection by the links 42. By way of example, the plurality of links 42 provided preferably should exceed three or more as for example all of the major elements 23 can be interconnected by the links 42. However, it should be appreciated that if desired, a fewer number of major elements can be interconnected as for example alternate sets of major elements. Also it should be appreciated that the links 42 rather than being S-shaped can have any other desired configuration in order to provide the desired length to facilitate expansion of the segments 12 of the stent 11 as hereinafter described in deployment of the stent.

It can be seen by utilizing the construction shown that various lengths of stents can be readily provided merely by providing additional segments 12 with interconnecting links 42. Thus stents ranging in size from 1 to 10 mm can be utilized for treating small lesions. Medium length stents can range from 10 to 18 mm and longer stents ranging from 18 to 36 mm can be provided for use in saphenous vein grafts or in diffused or long lesions.

Radiopaque markers 51 of the type described in copending application Ser. No. 08/991,378 filed Dec. 16, 1997 are provided in openings 52 in the pattern 21 of the stent 11 to facilitate positioning of the stent during deployment as hereinafter described.

Figure 2:
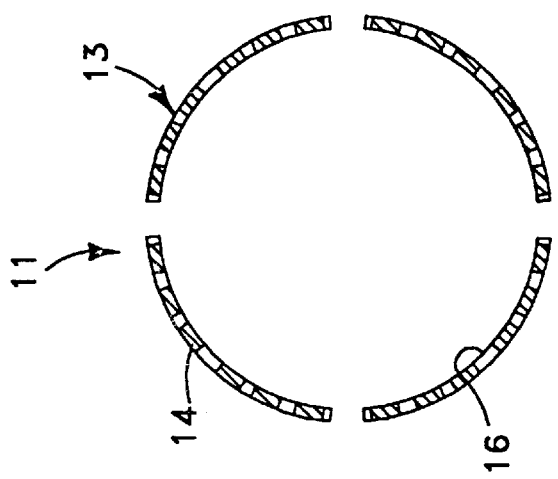
FIG. 2 is a cross-sectional view taken along the line 2—2 of FIG. 1.
Figure 3:
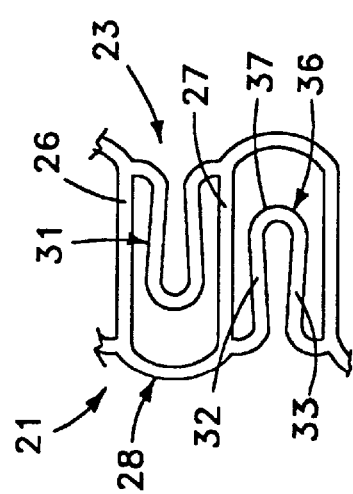
FIG. 3 is an illustration showing a portion of the pattern of the stent in FIG. 1.

Operation and use of the stent hereinbefore described may now be briefly described as follows. Let it be assumed that the stent 11 is to be deployed in a conventional manner into a vessel of the heart in connection with a conventional balloon angioplasty treatment in which a balloon is utilized to create a larger flow passage through a stenosis in the vessel. With the same or a different catheter, a stent typically is carried by a deflated balloon on the catheter and when the stent is appropriately positioned by the use of the radiopaque markers 51, the balloon on the catheter is expanded to cause expansion of the stent 11 by simultaneously expanding the segments 12 through which the balloon on the catheter extends. By utilizing a plurality of radiopaque markers 51 extending longitudinally of the stent as well as circumferentially of the stent, it is possible as explained in copending application Ser. No. 08/991,378 filed Dec. 16, 1997 to ascertain how the stent 11 is expanding in the vessel. When the stent 11 has been expanded from its initial contracted position as for example a diameter of 0.060" or 1.5 mm to an expanded position as shown in FIG. 2 to 3.5 mm, as can be seen in FIG. 2, the sinusoidal patterns of the segments are expanded circumferentially. As this occurs the open sides of the major elements 23 expand to such an extent that the minor elements 36 are opened up to unfold the folded struts 31 so that they are substantially straight as shown in FIG. 2 to form the third strut of the triangularly-shaped truss member 28. Thus, there is provided a plurality of serially connected truss members extending circumferentially of the stent 11 and in effect forming a truss 57 (see FIGS. 3 and 4) extending circumferentially of the stent. Thus it can be seen that each of the segments 12 has a pattern 21 which when expanded forms a continuous truss extending circumferentially of the segment 12 and stent 11.

As the serially connected truss members 56 are being formed into the truss 57, there is a shrinkage in length of the segments 12 in a direction of the longitudinal axis 22. This shrinkage is compensated by expansion of the flexible expansible S-shaped links 42 so that the stent has an overall length which remains substantially the same.

After the stent 11 has been expanded to the desired circumference, the balloon used for the expansion can be deflated and thereafter removed in a conventional manner leaving the stent in place in the stenosis in a vessel to retain the flow passage through the stenosis in an open condition.

It should be appreciated that if desired, the stent 11 still has advantageous features even if the stent is not completely expanded to its full size so that the strut 56 is not completely straight to provide increased radial strength.

The stent 11 constructed in the manner shown provides a stent which has a high degree of flexibility to permit its advancement through tortuous vessels and which after being deployed and expanded as hereinbefore described has a high radial strength. The sinusoidal pattern 21 which is provided makes it possible to expand the stent with relatively low inflation pressures in the expansion balloon as for example below four atmospheres while providing a stent which has a very high radial strength. This high radial strength of the stent is important in a number of applications for stents. For example it is particularly advantageous where it is necessary to place stents in highly calcified stenoses which frequently occur in the ostium of the left or right coronary artery.

Figure 5:
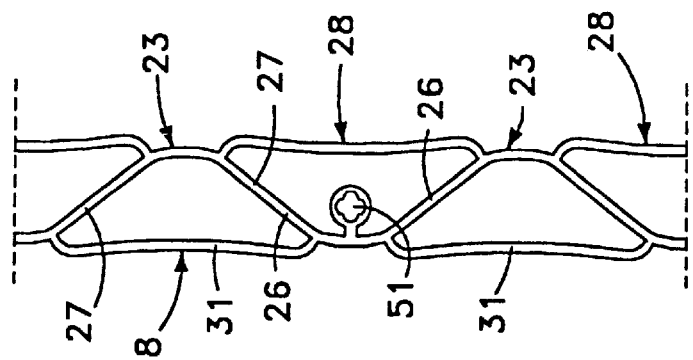
FIG. 5 is an illustration showing a portion of the pattern of the stent shown in FIG. 3 and how a plurality of three-sided truss members are formed to provide a truss to provide high radial strength.
Figure 6:
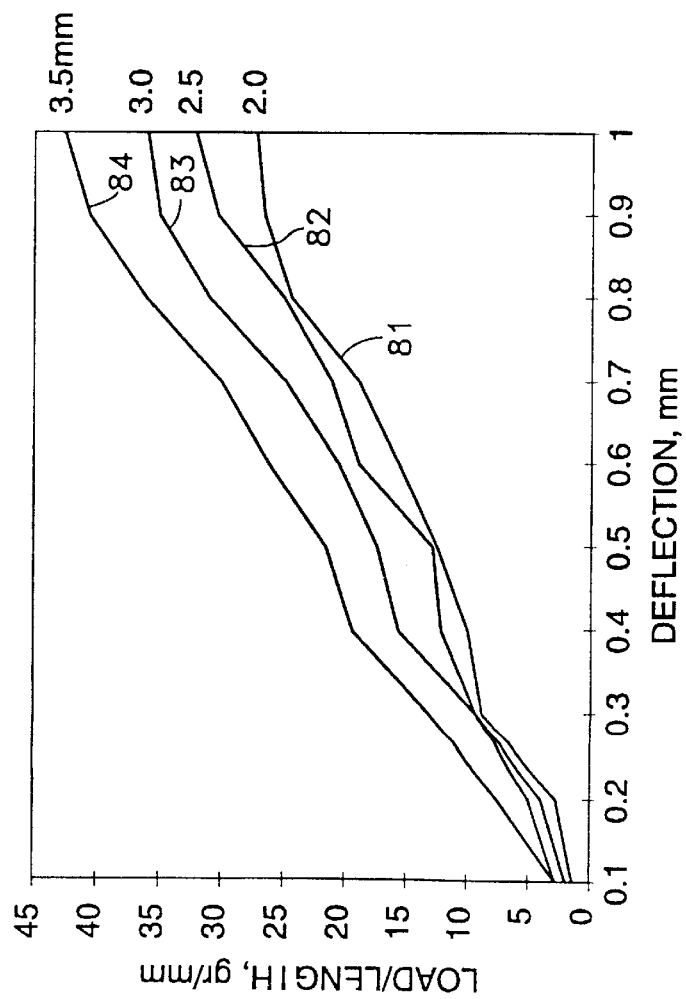
FIG. 6 is a graph showing the results of a three point compression test for stents incorporating the present invention.
Figure 7:
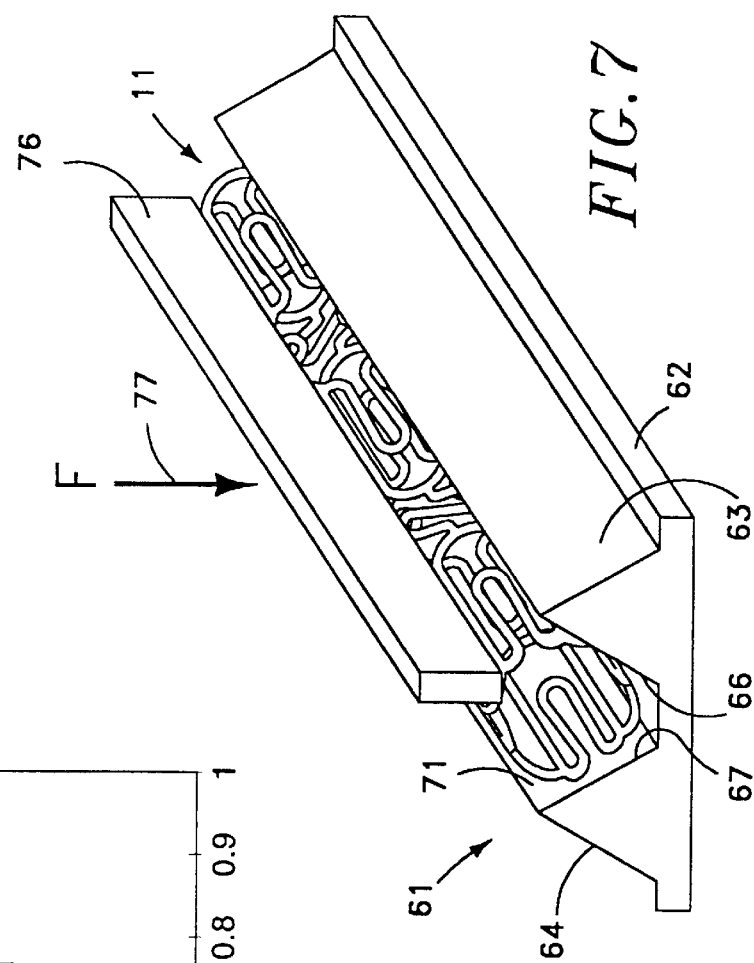
FIG. 7 is a diagrammatic illustration of a test fixture used for obtaining the test results shown in FIG. 6.

The high radial strength of stents incorporating the present invention have been analyzed as shown in FIG. 5 with a three point compression test utilizing the fixture 61 which is shown in FIG. 6. The fixture 61 consists of a rectangular base 62 which has mounted thereon and secured thereto two spaced-apart parallel bars 63 and 64 which are triangular in cross section. The two bars 63 and 64 provide two upwardly and outwardly inclined surfaces 66 and 67 that are spaced apart sufficiently so that a stent 11 (hereinbefore described) can be disposed in the longitudinally extending recess 71 defined by the two surfaces 66 and 67. The recess 71 is sized so that the stent 11 will engage the surfaces 66 and 67 but is spaced above the surface of the base plate 62 so that forces applied to the stent by a longitudinally extending bar 76 overlying the stent 11 are received by the surfaces 66 and 67. Thus three longitudinally extending line contacts spaced apart by approximately 120° are provided to provide a three point compression test for the stent to measure the compressive forces applied to the stent 11 and to thereby ascertain the radial strength of the stent. The force applied to the bar 76 and being measured is indicated by an F arrow 77. The force applied is measured as well as the deflection which occurs by a conventional gauge.

Figure 4:
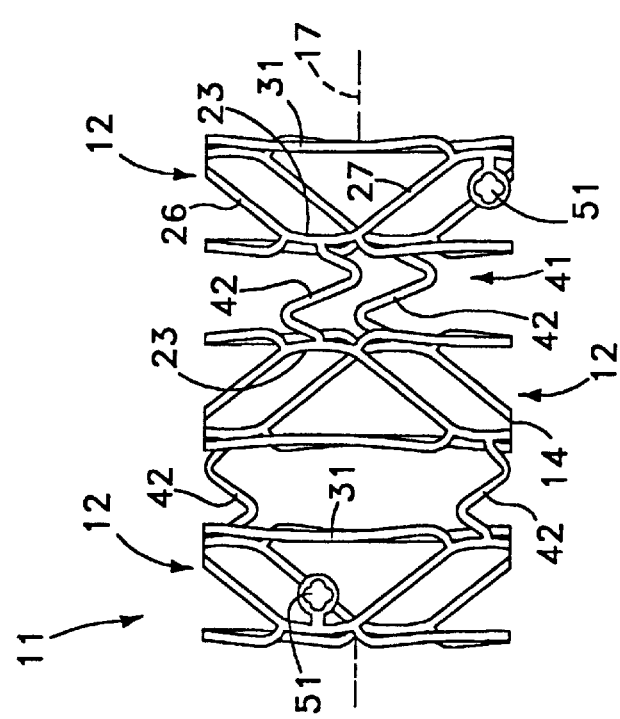
FIG. 4 is a side elevational view showing the stent in FIG. 1 in an expanded position.

The results of the measurements made with the fixture shown in FIG. 6 are shown in FIG. 4 in which the deflection in millimeters is shown on the abscissa and in which the load per length is expressed in grams per millimeter on the ordinate. Thus the ordinate shows the force applied at each $\frac{1}{10}$ mm of the stent along the longitudinal axis of the stent. The stent 11 was compression tested at four different expansion diameters at 2 mm, 2.5 mm, 3 mm and 3.5 mm. The curves of these four diameters are respectively 81, 82, 83 and 84. The stent 11 utilized in the tests had the following dimensions:

Length—16 mm

Unexpanded diameter—1.5 mm

Crimped diameter (after crimping on balloon)—0.8 mm

Expanded diameter—3.5 mm

The test was conducted with the stent having an expanded diameter of 3.5 mm.

In connection with the graph shown in FIG. 5, in order to compare the performance of different length stents, the forces applied have been normalized to a force per millimeter to make possible comparison of different lengths of stents regardless of their length. The force F was applied by the use of a conventional gauge which has a vertical travel caliper as well as a force gauge in which the force is displayed in grams and the vertical travel is displayed in thousandths of an inch or in fractions of millimeters.

As can be seen from the graph in FIG. 5, the stent of the present invention has a high radial strength which is achieved principally by the use of the folded struts 31 provided in the major elements 23 of the sinusoidal pattern. Under compressive forces, the deflection is substantially linear regardless of the length utilized. This much greater radial strength is achieved principally because of the use of the folded struts 31. This high radial strength is achieved without sacrificing the amount of force required to expand the stent. Thus with the present stent it has been found that the expansion forces required for expanding the stent are substantially no greater than without the use of the folded struts and that the use of the foldable struts increases the radial strength by at least two times.

In view of the foregoing it can be seen that there has been provided a stent which is very flexible along its length and which can be provided in various lengths. It can be readily expanded and when expanded has high radial strength. Also it substantially maintains its length as it is expanded even though the segments forming the stent shrink.

What is claimed:

1. An expandable stent for deployment into a vessel having a lumen therein comprising a cylindrical member having a length and having proximal and distal extremities and being formed of a metal having a wall defining a central bore having a longitudinal axis extending from the proximal extremity to the distal extremity, said cylindrical member having an inside diameter and an outside diameter, said cylindrical member being formed of at least one cylindrical segment, said at least one cylindrical segment having a pattern formed therein which when the stent is expanded is capable of forming a truss formed of serially connected three-sided triangularly-shaped truss members, said pattern including a first sinusoid extending circumferentially through 360° about the longitudinal axis, said first sinusoid being in the form of a plurality of major elements having first and second interconnected struts having respectively first and second lengths forming first and second sides of the truss members and defining open sides therebetween, alternate major elements having therein open sides facing in opposite directions, said pattern also including a plurality of foldable struts disposed within the open sides of the major elements and secured to the first and second struts of the major elements, and when the stent is expanded, being capable of unfolding to form the third sides of the truss members, said truss members being serially connected to form a continuous truss extending circumferentially of the cylindrical member to provide a stent which when expanded has high radial strength.

2. An expandable stent as in claim 1 wherein the stent is comprised of a plurality of segments and further including expansile interconnection means for interconnecting the segments so that as the segments are expanded and shrinkage occurs, the expansile interconnection means expands to accommodate the shrinkage so that there is substantially no change in length of the stent during expansion.

3. An expandable stent as in claim 2 wherein said expansile interconnection means is in the form of folded links.

4. An expandable stent as in claim 3 wherein said folded links are S-shaped.

5. An expandable stent as in claim 1 wherein said major elements are substantially U-shaped.

6. An expandable stent as in claim 1 wherein said plurality of folded struts are in the form of minor elements having first and second interconnected legs having respectively first and second lengths.

7. An expandable stent as in claim 1 wherein said minor elements are substantially U-shaped and form a second sinusoid.

\* \* \* \* \*